United States Patent [19]
Claxton, III et al.

[11] Patent Number: 4,998,534
[45] Date of Patent: Mar. 12, 1991

[54] BLOOD PRESSURE MONITOR WITH COMPENSATION FOR PHYSIQUE AND METHOD OF USE

[75] Inventors: Philander P. Claxton, III, Rockville, Md.; George L. McDade; Jon D. Schaffer, both of Knoxville, Tenn.

[73] Assignee: Medical Devices Limited Partnership, Rockville, Md.

[21] Appl. No.: 422,816

[22] Filed: Oct. 19, 1989

[51] Int. Cl.5 .................................... A61B 5/0205
[52] U.S. Cl. .................................. 128/670; 128/681; 364/413.03
[58] Field of Search ............ 128/677, 671, 668, 672, 128/681, 682, 637, 668, 670, 671, 672, 677, 680, 681, 682; 364/413.02, 413.03

[56] References Cited
U.S. PATENT DOCUMENTS
4,501,280  2/1985  Hood ................................ 128/677

FOREIGN PATENT DOCUMENTS
2541887  9/1984  France .......................... 128/670

Primary Examiner—William E. Kamm
Assistant Examiner—Robert L. Nasser, Jr.
Attorney, Agent, or Firm—Lowe, Price, LeBlanc, Becker & Shur

[57] ABSTRACT

An automated blood pressure measurement apparatus and method which includes an inflatable cuff at a predetermined height relative to where a user must sit or stand in order to comfortably use the apparatus including a correction arrangement which provides a numerical correction for a hydrostatic pressure differential between the heart level of a user in a posture implied by the predetermined height of the cuff based on the user's overall height and a standard posture for measuring blood pressure at which the cuff height is at approximately the same level as the heart level when blood pressure is measured.

13 Claims, 11 Drawing Sheets

BLOOD PRESSURE MONITOR WITH COMPENSATION FOR PHYSIQUE AND METHOD OF USE

TECHNICAL FIELD

This invention relates to devices for determining physical condition. In particular, this invention relates to automated blood pressure testing apparatus for use by the public and specifically to devices of that type which include the facility of providing a correction for variations in physique and/or posture of the user.

BACKGROUND ART

Blood pressure has long been known as an important factor in the evaluation of the general level of health of an individual. Blood pressure is typically measured by a so-called auscultatory method using a sphygmomanometer where an inflatable cuff is placed over an extremity of a subject and inflated to a pressure at which circulation is halted in the extremity and then deflated while the subject's pulse and circulation are aurally monitored with a stethoscope or the like. Since the inflatable cuff imposes pressure on the extremity against the natural elasticity of the flesh of the extremity, the circulation in different depths below the surface of the flesh in the extremity will be affected at different pressures. Upon deflation after circulation is halted in the extremity, circulation will resume in deep tissues at a first pressure, referred to as the systolic pressure, reflecting the maximum pressure developed by the heart and at a second, lower pressure, known as the diastolic pressure, in the shallow tissues near the surface of the extremity which reflects the minimum pressure against which the heart must work.

When the above procedure is performed, it is necessary for it to be performed by a person other than the person whose blood pressure is being measured since muscular tension necessary to control deflation of the cuff or to position a listening device such as a stethoscope will affect the accuracy of the measurement. Also, the ability to hear the differences in circulation will be reduced, since circulation in the ear of the user will mask the subtle changes in the sounds caused by changes in circulation in the extremity during control thereof by the inflatable cuff.

In recent years, the increase in "health-consciousness" on the part of some individuals has led to the development of personal automated devices for measuring blood pressure and pulse rate. While the cost of such devices is not great and their availability is reasonably widespread, such devices are likely to be regarded as unnecessary or a luxury for private ownership unless strongly recommended by a physician having already diagnosed hypertension in the individual. Thus, such devices are not likely to result in the discovery of hypertension or other conditions for which treatment should be sought.

On the other hand, it has become increasingly apparent in recent years that hypertension, or elevated blood pressure, is a major, generally undiagnosed, condition since it is not accompanied by symptoms which would typically lead an individual to seek medical attention. Over a period of time, undiagnosed or untreated hypertension may cause substantial damage or degeneration to the heart and circulatory system. Such undiagnosed and/or untreated hypertension has been found to be a major factor in the development of heart disease or the occurrence of heart attacks. Further, abnormal blood pressure may be a major indicator of the existence of an aneurism, an enlargement of a blood vessel which has an increased likelihood of bursting with often catastrophic consequences and high mortality rate.

To provide such availability of blood pressure testing, it has become common for medical institutions such as hospitals to provide screenings for high blood pressure and other conditions. Such screenings have the advantage of providing trained personnel to test and counsel large numbers of people. However, such screenings are expensive to the institution providing them and involve administrative and other expenses such as advertising and publicity. While such screenings have been fairly successful at raising public awareness of particular health problems, they often do not succeed in promoting follow-up testing or treatment, particularly where the physical parameter tested is subject to wide variation due to many causes, as is the case with blood pressure. Further, there may be a perceived lack of confidentiality in such screenings and the potential adverse effects of seeking information concerning hypertension on insurance premiums may deter an individual from seeking information concerning his or her condition.

Accordingly, it has recently become apparent that there is a need for the ready availability to the public of apparatus to measure blood pressure. Such availability provides the equivalent of screening by trained personnel, which, while generally accurate and offering the possibility of providing advice and counseling when results are abnormal, suffers from the drawbacks of expense, irregular and inconvenient availability, a perceived lack of privacy and confidentiality and the likelihood that a significant result will be dismissed by the subject due to the unusual circumstances of the screening itself. It is also well-known that hypertension cannot be reliably diagnosed on the basis of a single blood pressure measurement but requires several consistently high measurements to reliably indicate the condition.

Even after diagnosis of hypertension, it is necessary to periodically monitor blood pressure. The expense or inconvenience of obtaining such measurements may impede or interfere with treatment. Even the personal blood pressure monitors alluded to above may constitute a relatively large expense and an alternative to ownership of such a device is necessary.

Recently, therefore, it has been found to be effective in the early detection of hypertension to provide automated blood pressure testing apparatus in public places either as a public service or on a pay-per-use basis. This has been found to be particularly effective in pharmacies and other commercial establishments which also distribute prescription medications because of the availability of a pharmacist who can give independent confirmation of the need to consult a physician if blood pressure measurements are consistently high. Installation of such automated blood pressure measuring devices has also been found to be beneficial to the commercial establishments providing them and such installations have proven to be a substantial source of income when installed on a pay-per-use basis as well as enhancing sales of other products. Such installations allow blood pressure tests to be done conveniently and at intervals over a substantial period of time and with a fairly high degree of confidentiality.

One example of a suitable device is disclosed in U.S. Pat. No. 4,729,382, filed on Sept. 2, 1986, and issued to joint inventors herein Jon D. Schaffer and George L. McDade entitled METHOD AND APPARATUS FOR AUTOMATICALLY DETERMINING PULSE RATE AND DIASTOLIC AND SYSTOLIC BLOOD PRESSURE which disclosure is fully incorporated by reference herein. Details of the operation of the basic device which are not necessary to a full understanding of the present invention are omitted herein in the interest of clarity and full disclosure of such details may be found in the patent incorporated by reference.

With regard to the basic device, it has been found that, for installation in a commercial establishment, a stand is desireable due to the high cost of floor space. Further, and for the same reason, it has been found desireable to provide such a stand which allows the basic device to be used when the user is in a standing position. Use in a standing position is also desireable since the device can be used less conspicuously in a store environment where it is unusual for a customer to sit. However, such an installation presents a problem since the standing posture of a user is not typical of standard postures in which blood pressure is commonly measured. Specifically, when done by medical personnel, blood pressure is typically measured at the upper arm with the subject either seated or recumbent so that the inflatable cuff used in the measurement will be located at heart level. It is highly desireable, in this regard, considering potential use by users who may be screening themselves for hypertension and those who use the device as an aid to medical treatment that the measurements made by the device be accurately and consistently correlated with measurements made by trained medical personnel using sphygmomanometers. It has also been found to be desireable that the inflatable cuff be rigidly mounted to the housing of the device as shown in U.S. Patr. Des. No. 298,167, filed Dec. 6, 1985, and also issued to joint inventors herein Jon D. Schaffer and George L. McDade. This arrangement provides for protection of pneumatic parts which are vulnerable to tampering and vandalism and permits the pressure cuff, pump and valves to be assembled in a module which can be readily replaced for ease of servicing in the field. The device is also intended to take blood pressure measurements from the forearm of the user which has been found to be highly accurate in accepted invasive methods of blood pressure measurement using an arterial catheter. Use of the forearm of the user for blood pressure measurements is also a matter of convenience to the user, particularly in the intended application, since a comfortable and natural posture can be maintained which does not draw attention to the user. For much the same reasons, and also the additional fabrication and possible maintenance expense involved, it is not deemed to be reasonably practical to provide for alteration of the height of the entire machine in an attempt to standardize posture since that effect would not be achieved in any event without substantial other structure impeding ease and discreteness of use. Further, use of the forearm does not require the upper arm to be exposed and therefore does not require sleeves to be fully rolled up, thus avoiding the binding effect of clothing which may affect measurement results. However, unlike techniques using the upper arm, the cuff is not assured to be at or near heart level and, therefore, errors due to differences in hydrostatic pressure due to the difference in height between the heart and the inflatable cuff may cause substantial differences between the actual measurement made and the value which would have been obtained if the subject were in a more standard position or posture for measurement of blood pressure.

DISCLOSURE OF THE INVENTION

Accordingly, it is an object of the invention to provide a method of correcting for differences in hydrostatic pressure caused by differences between the levels of the user's heart and that of the inflatable cuff during blood pressure measurement during use of an automated blood pressure measurement apparatus.

It is another object of the invention to provide a correction method for correction of blood pressure measurements for hydrostatic pressure errors based on a parameter which would be readily known to the user or which can be easily sensed.

It is a further object of this invention to provide a blood pressure measurement apparatus which determines the posture of the user in a discreet, comfortable and natural manner and permits correction for hydrostatic pressure differential to be made in a simple and straightforward manner.

It is yet another object of the invention to provide an improvement in an automated blood pressure measurement apparatus which occupies little floor space even when in use but will provide an output which is accurately correlated with blood pressure measurements made in standard postures by the use of auscultatory techniques and sphygmomanometers operated by trained personnel.

Therefore, in accordance with one aspect of the invention, a method is provided comprising the steps of operating a data entry means to enter data corresponding to the height of a user, inserting the lower arm of the user within an inflatable cuff, causing an apparatus to measure the blood pressure of the user, and correcting the measurement result in accordance with the height of the user to derive a corrected result.

In accordance with another aspect of the invention, a method is provided comprising the steps of establishing a correction relationship between at least average heights of heart levels relative to user heights and a predetermined height of an inflatable cuff and measured blood pressure values measured in a standard posture, obtaining data representing the height of a user, measuring the blood pressure of the user to derive a measurement result, and correcting the measurement result according to the correction relationship to obtain a corrected measurement value.

In accordance with a further aspect of the invention, an apparatus is provided comprising an inflatable cuff for encircling a portion of a user and mounted at a predetermined height relative to a support for said user, a controllable fluid pump apparatus for controllably inflating and deflating the inflatable cuff, pressure measuring apparatus responsive to variations in pressure in the cuff during said inflating and deflating thereof and providing a measurement result, a device for providing data representing an overall height of the user, an apparatus for providing a correction relationship between average blood pressure of a typical user in a predetermined posture determined by the height of the user and the predetermined height of the inflatable cuff and a standard posture, and apparatus for correcting said measurement result based upon said overall height data of said user and said correction relationship and providing a corrected measurement value.

In accordance with yet another aspect of the invention, an improvement comprising a data entry device for inputting data representative of a parameter of the physique of the user and including a device responsive to the data entry means for applying a correction to the output of a measuring means to correct the output thereof is provided for an automated blood pressure measurement apparatus.

The attainment of the above and other objects of the invention will become apparent to those skilled in the art in light of the following detailed description of the invention in connection with the attached drawings which will fully enable any person skilled in the art to make and use the same.

BEST MODE FOR CARRYING OUT THE INVENTION

Figure 1:
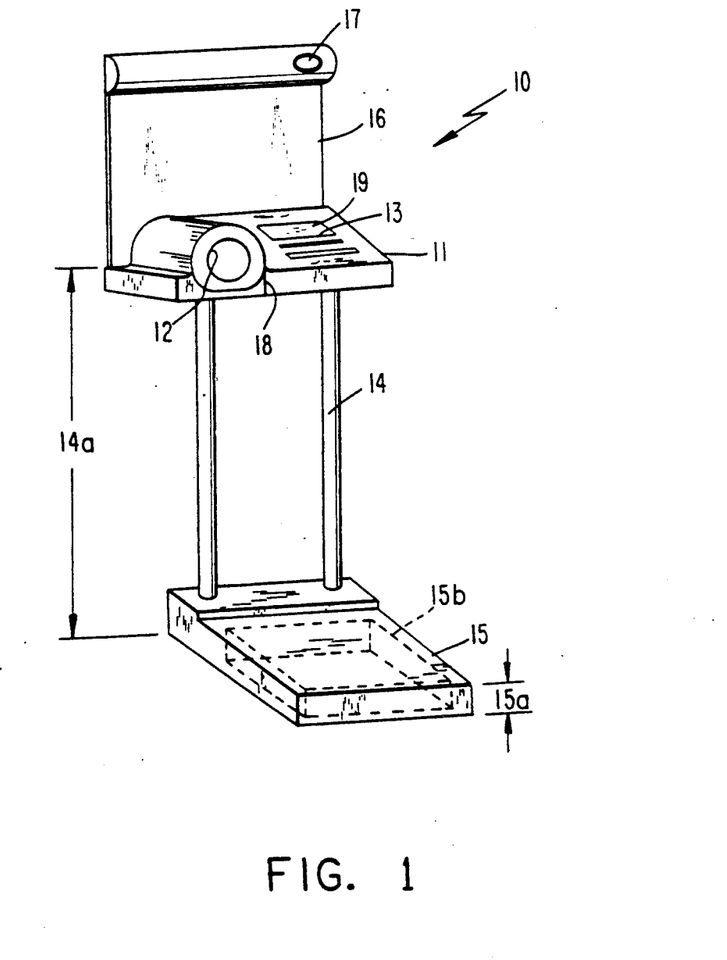
FIG. 1 is a perspective drawing of the automated blood pressure measurement apparatus comprising the invention.

FIG. 1 shows the overall appearance of the apparatus according to the invention. The physical arrangement of the invention 10 includes a base 15 which can advantageously include a scale 15b for measuring the weight of the user. Housing 11, including a mounting position for an inflatable cuff 12, a display, which is preferably digital in nature, and keyboard 13 is supported on posts 14. Panel 16 can be used to display written instructions, blood pressure information and interpretive data or even advertising matter for perusal by the user during operation of the blood pressure testing apparatus. The housing 11 may advantageously be made in a divided manner as illustrated at division 18 so that the pump, valves, cuff and pressure sensors are contained in a single module for ease of service and field replacement. While the entire unit, constructed according to the invention, has been found to be of relatively light weight and easily portable, the overall size of the device may be somewhat awkward to move when relocation is required, and wheels (not shown) may be provided at one edge of the base to allow the device to be tilted and rolled on the wheels but stable and stationary when upright. The configuration of the base is not critical and dimension 15a is typically determined to accommodate a treadle for a scale, as noted above. If a scale is not included, the base may be of any desired construction, such as that illustrated in FIGS. 2A–2C, which will offer good stability and rigidity and may permit the user to stand on the floor upon which the invention is also placed.

Speaker 17 can be used for messages or instructions in any desired language and for voice-synthesized reporting of the test results, if desired, in a manner well known in the art. In the preferred embodiment, such voice data is held in read-only-memory for rapid access, freedom from mechanical and aging deterioration (as compared, for instance, to tape) and rapid interchange of messages (for other languages, for instance) if desired. This feature is also advantageous for use of the apparatus by the blind or visually impaired. Location of speaker 17 is not critical to the practice of the invention and can be located at any position deemed convenient.

Posts 14 extend through base 15, of whatever form may be chosen, and terminate at approximately floor level. Due to the flexure angle of the human elbow, the apparatus is arranged and the post length determined to place the cuff 12 at a level which is at heart level for a user several inches shorter than average human height. The dimension adopted in the preferred embodiment of the invention accommodates a user of a minimum height of 64 inches. This design feature has the advantage that all blood pressure corrections for taller (or slightly shorter, as will be discussed below) persons will be done by a subtraction of hydrostatic pressure, thus simplifying the programming of microprocessor 20. It has also been found that using software to provide a set of corrections for a specific height of cuff 12 is sufficiently simple that custom adaptations to different cuff heights may be easily done if necessary. Therefore, for the predominant number of installations it has been found economical to standardize heights of posts 14 and to provide different corrections in software for the thickness 15a of base 15, if, in fact, the base is used to support the user during blood pressure testing.

Housing 11 may also be advantageously adapted to be easily removable from posts 14 so that persons of shorter stature may be accommodated with housing 11 placed on another support which will allow such a user to assume a nearly standard blood pressure measurement posture, in which case, the default user height value of 64 inches will yield an accurate result regardless of the actual height of the user. Alternatively, a user of short stature may be supported by a base or other support arrangement to a height where a standard posture is approximated.

Finally, it is noted that the preferred form of housing 11 is also not critical to the practice of the invention and details thereof are omitted in the interest of clarity. However detailed illustration of a preferred form of the housing are fully illustrated in U.S. Pat. Des. No. 298,167, cited above and hereby incorporated by reference for purposes of full, detailed illustration of the housing 11.

Figure 2A:
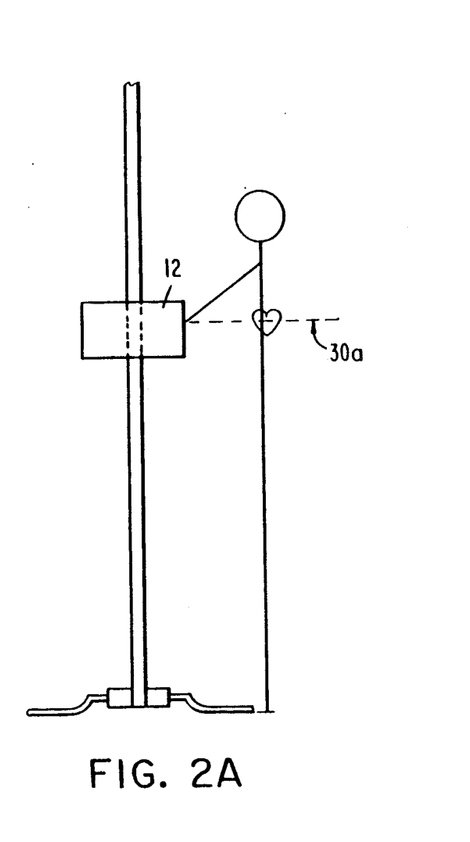
FIGS. 2A, 2B and 2C illustrate the use of the invention by users of different heights and the manner in which a user's posture is determined by the combination of user height and cuff height.
Figure 2B:
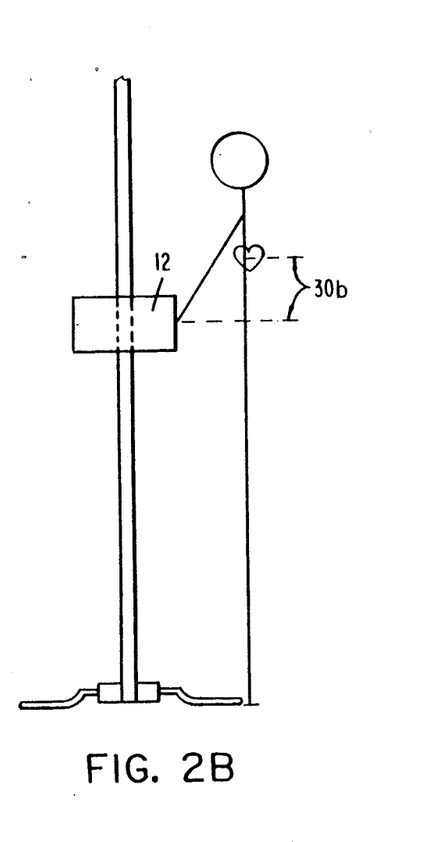
Figure 2C:
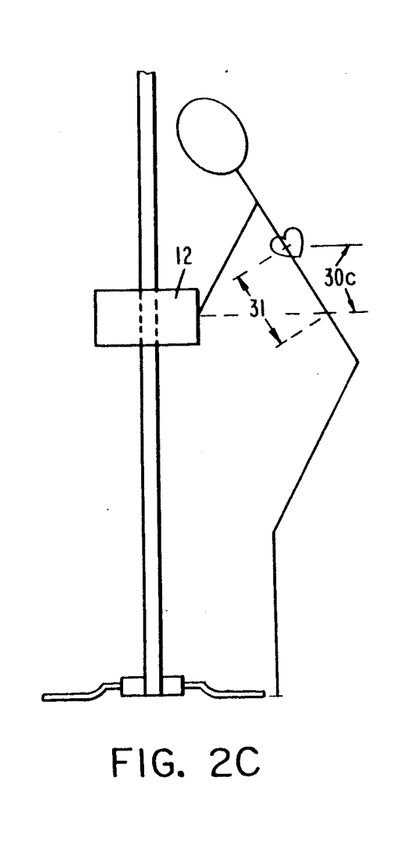

FIGS. 2A, 2B and 2C illustrate the use of the invention by users of differing heights. FIG. 2A shows use by a person of the minimum exemplary design height. In this case, the inflatable cuff is at heart level and the user assumes a comfortable, upright position with the user's forearm inserted in cuff 12. The upper arm assumes a comfortable upward angle to the user's shoulder. Also, in this case, no correction for hydrostatic pressure is required since the cuff is at heart level.

In FIG. 2B, the user is depicted as being of greater than minimum design height for the cuff position and the heart level will be above the center line of the cuff by a distance 30b. While the upper arm of the user rises at a sharper angle, this posture is still upright and comfortable. The height differential 30b will cause the measured blood pressure to be increased by the hydrostatic pressure corresponding to distance 30b and correction will be made by the invention in a manner which will be explained below.

FIG. 2C illustrates the use of the apparatus by a user much taller than the minimum height for which the apparatus is designed. In this case, if the user were standing upright, the heart level would be above the center line of the inflatable cuff by a distance 31. However, the user will assume the most comfortable position which is slightly bent at the knees and waist. Correspondingly, heart level for such an individual will be brought to a level which is a distance 30c above the centerline of the cuff which is less than distance 31 and, hence, a smaller correction will be necessary for distance 30c than for distance 31.

Comparing FIGS. 2A-2C, it is seen that a non-linear correction function may be advantageously employed and is, in fact, used in the preferred embodiment of the invention. This fact also effectively provides a limit of the maximum height for which correction will be required.

Figure 3:
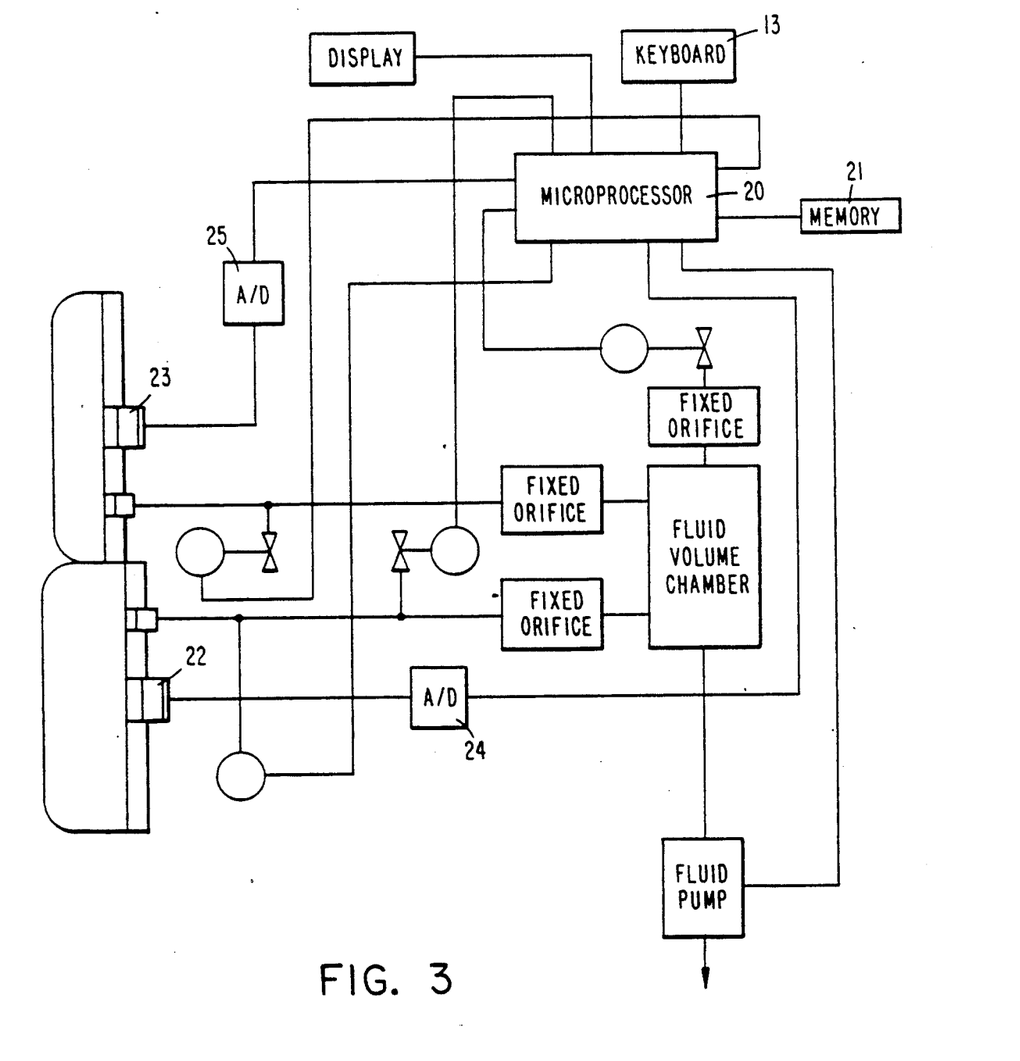
FIG. 3 is a schematic diagram of one embodiment of the invention.

FIG. 3 schematically illustrates a preferred embodiment of the invention. The figure is very similar to FIG. 1 of U.S. Pat. No. 4,729,382, cited and incorporated by reference above. Reference may be made to the disclosure of that document for details of the operation thereof.

Figure 5A:
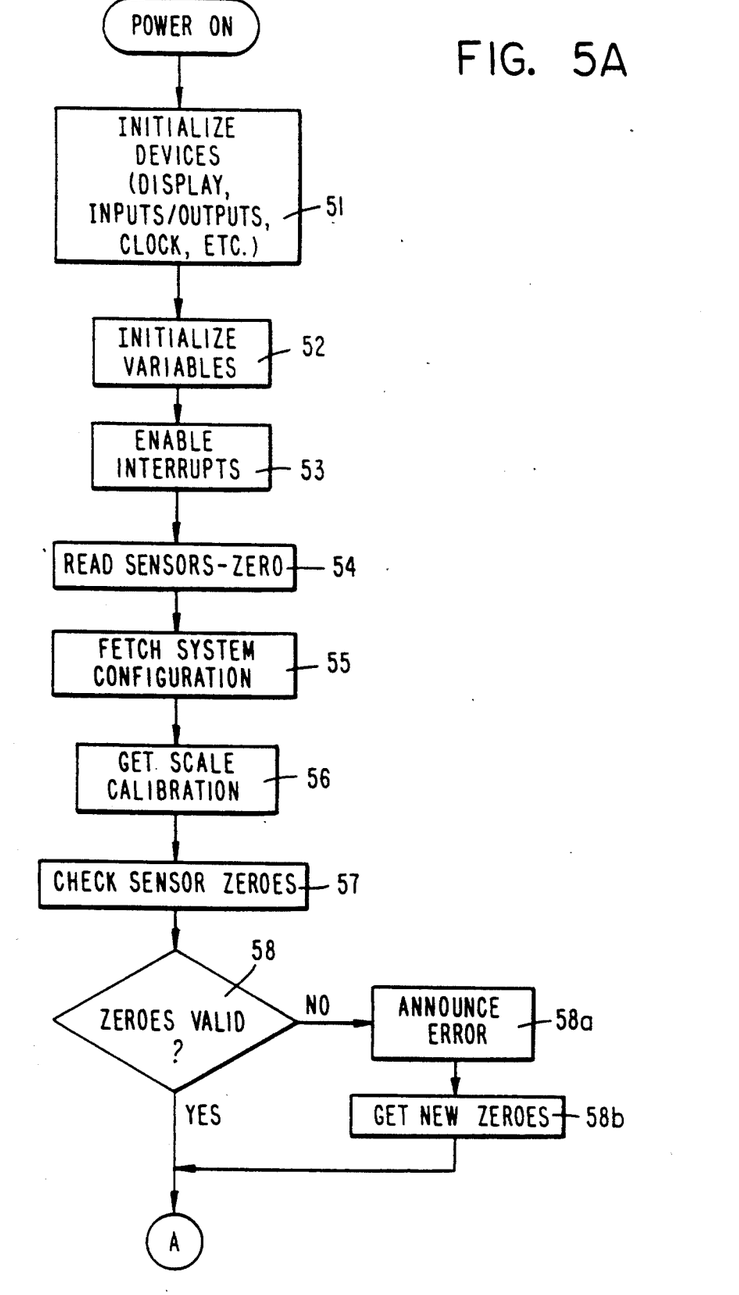
FIGS. 5A, 5B, 5C, 5D, 5E, 5F and 5G together comprises a flow chart indicating the programming of the microprocessor for carrying out the overall function according to the invention.

While the programming of the microprocessor, according to the present invention is deemed to be within the level of one skilled in the art, in view of the functions disclosed and the description of the operation of the invention given below, the basic microprocessor operations which are used in the practice of the invention will be explained with reference to the flow chart illustrated in FIGS. 5A-5G. As shown in FIG. 5A, upon energization of the apparatus of the invention, all peripheral devices, such as the display, inputs, outputs and clock, are initialized, as shown at 51. Subsequently, as is common in microprocessors, variables are initialized (52), interrupts are enabled (53) and sensors are read for zero valued output (54). Once this is done, memory is interrogated to obtain the user definable configuration of the apparatus. This step of obtaining the configuration, 55, is typically used to configure the apparatus for free use or pay-per-use operation. This step is also used to set defaults such as voice-synthesized prompts, language, etc.

Once the system configuration is established, the scale (if used) calibration is checked (56) and the sensor outputs are checked for zero-valued outputs (57). If these values are not within a predetermined range (58), a branch is taken to announce the error 58a and to obtain zero values 58b. If the sensor values have a zero value, the process continues.

Figure 5B:
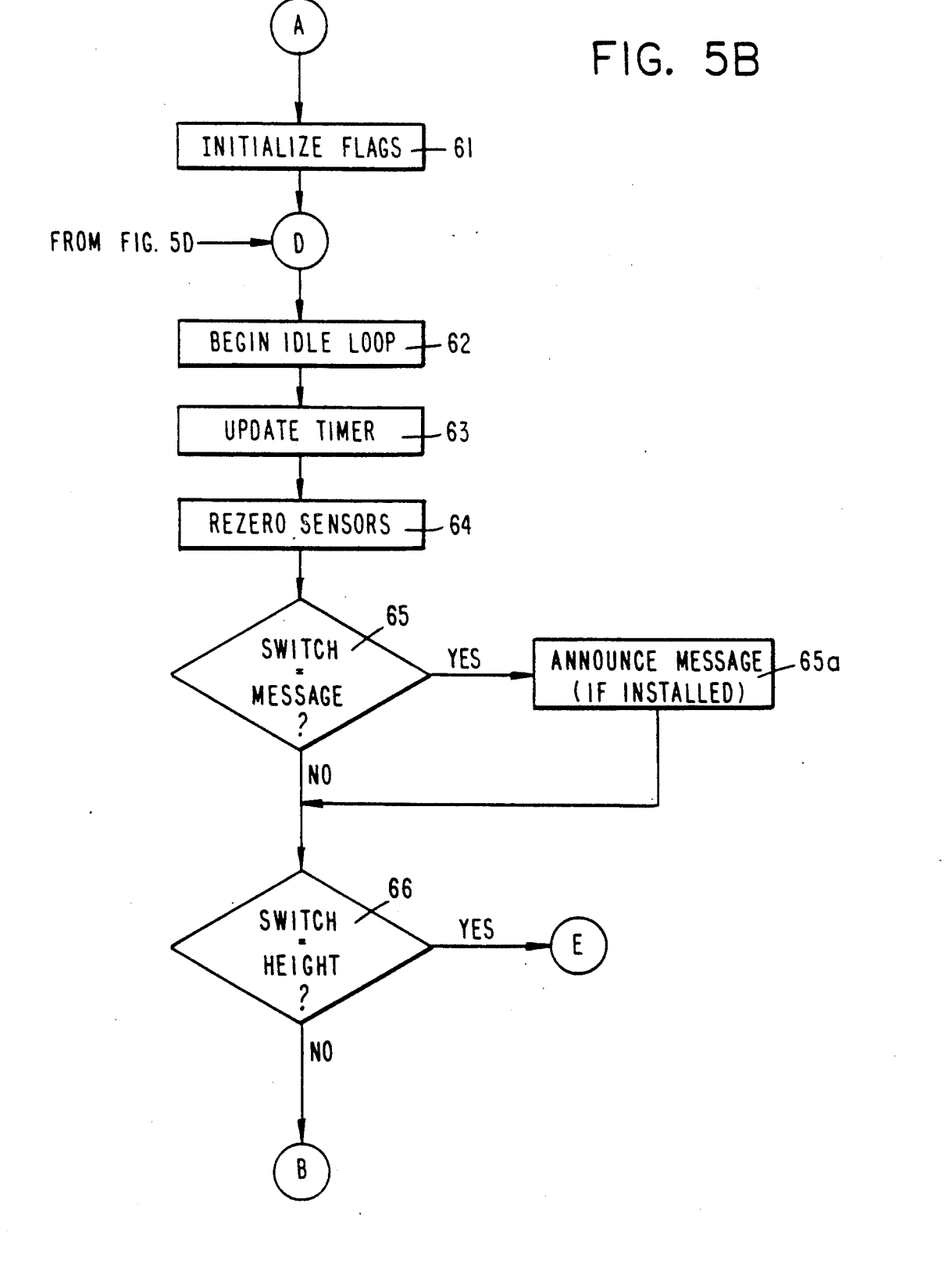

Referring now to FIG. 5B, flags in the microprocessor are initialized (61) and an idle loop is entered as designated by D and step 62. In this idle loop, the timers are periodically updated (63) and the sensors are rezeroed (64). After each performance of this check of inputs, the system is interrogated for a message (65) which may be installed as defined by the configuration of the system. This feature allows the apparatus to periodically draw attention of customers and to solicit use. If so, an announcement will be made by a voice annunciator or by display. Whether or not a message is installed, the process continues with an interrogation of the keyboard for an entry of user height data. If not, the idle loop continues at B.

Figure 5C:
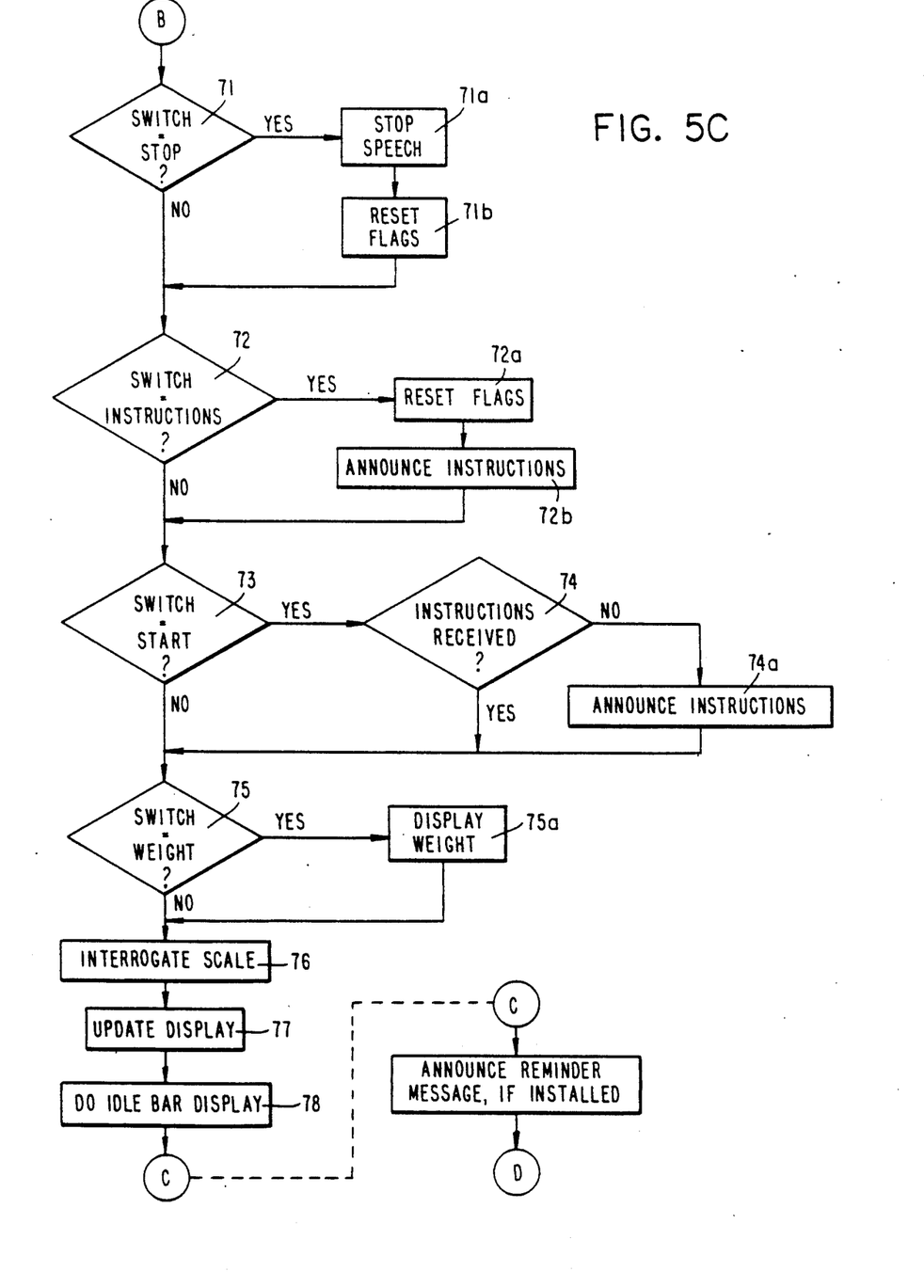

The following steps of the idle loop are shown in FIG. 5C. Step 71 interrogates a stop switch on the keyboard which interrupts any continuing speech synthesis or display and resets flags to effectively alter the default configuration of the apparatus as shown at 71a and 71b. The keyboard is then interrogated 72 to determine if a key has been actuated to request operating instructions for the apparatus. If so, default flags are reset and instructions are displayed or announced by voice-synthesis, as noted above. Then the keyboard is again interrogated 73 to sense depression of the start switch. If so, but no instructions are input 74, the user is again prompted to press the start switch 74a. After either of conditional branches 73 or 74 is performed, the process continues with further interrogation of the keyboard to determine if a weight inquiry has been made 75. If so, a subroutine 75a is entered to display the weight data, if requested, after which the weight data and display are again updated 76, 77 and the idle display is resumed and a reminder message concerning the blood pressure test capability of the apparatus is given. After the reminder message or if the weight display is not selected, the idle loop resumes at D of FIG. 5B.

Figure 5D:
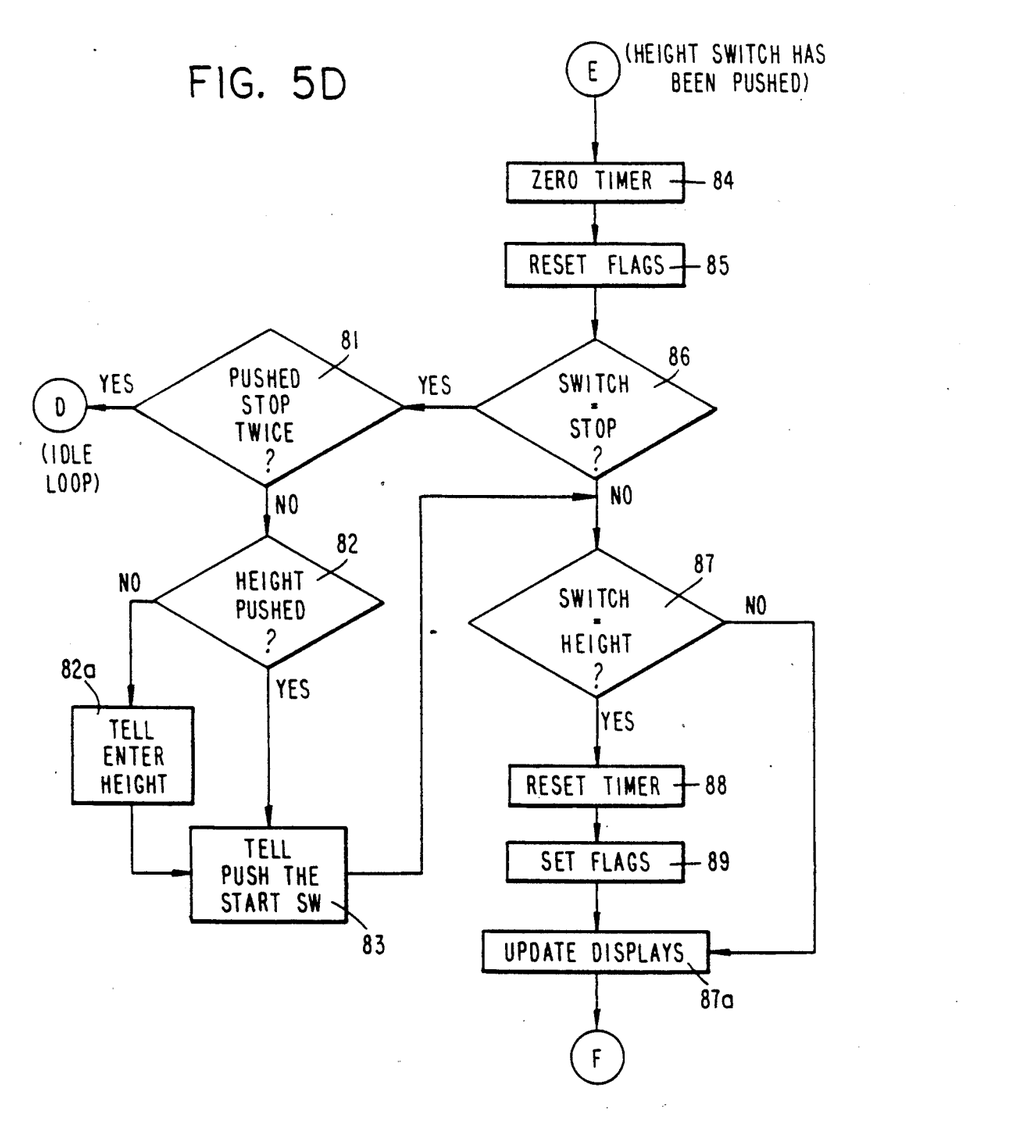

In the idle loop, if the interrogation of the keyboard at 66 to determine a height entry is successful, a branch is made to the procedure illustrated at FIG. 5D, as indicated by legend E. Upon taking this branch, the timer for the blood pressure (and pulse) test is reset to zero 84 and flags are reset 85 for the blood pressure test. At this point, the stop switch is interrogated to allow a user to abort the test at an early stage thereof. This early opportunity to abort the test is deemed to be helpful in instilling confidence of the user. This procedure also is a conditional aborting of the test since step 81 requires two actuations of the stop switch to return the system to the idle loop at D in FIG. 5B. If the stop switch has been pressed only once, flags are interrogated to determine if height data has been entered 82. If not, a prompt is given to enter height data. Afterwards or if height data has been entered previously, a prompt to press the start switch is given. If height data has been entered at this point, the timer and flags are reset 88, 89 in anticipation of resuming the test. In either case, displays are reset and the procedure continues at F.

Figure 5E:
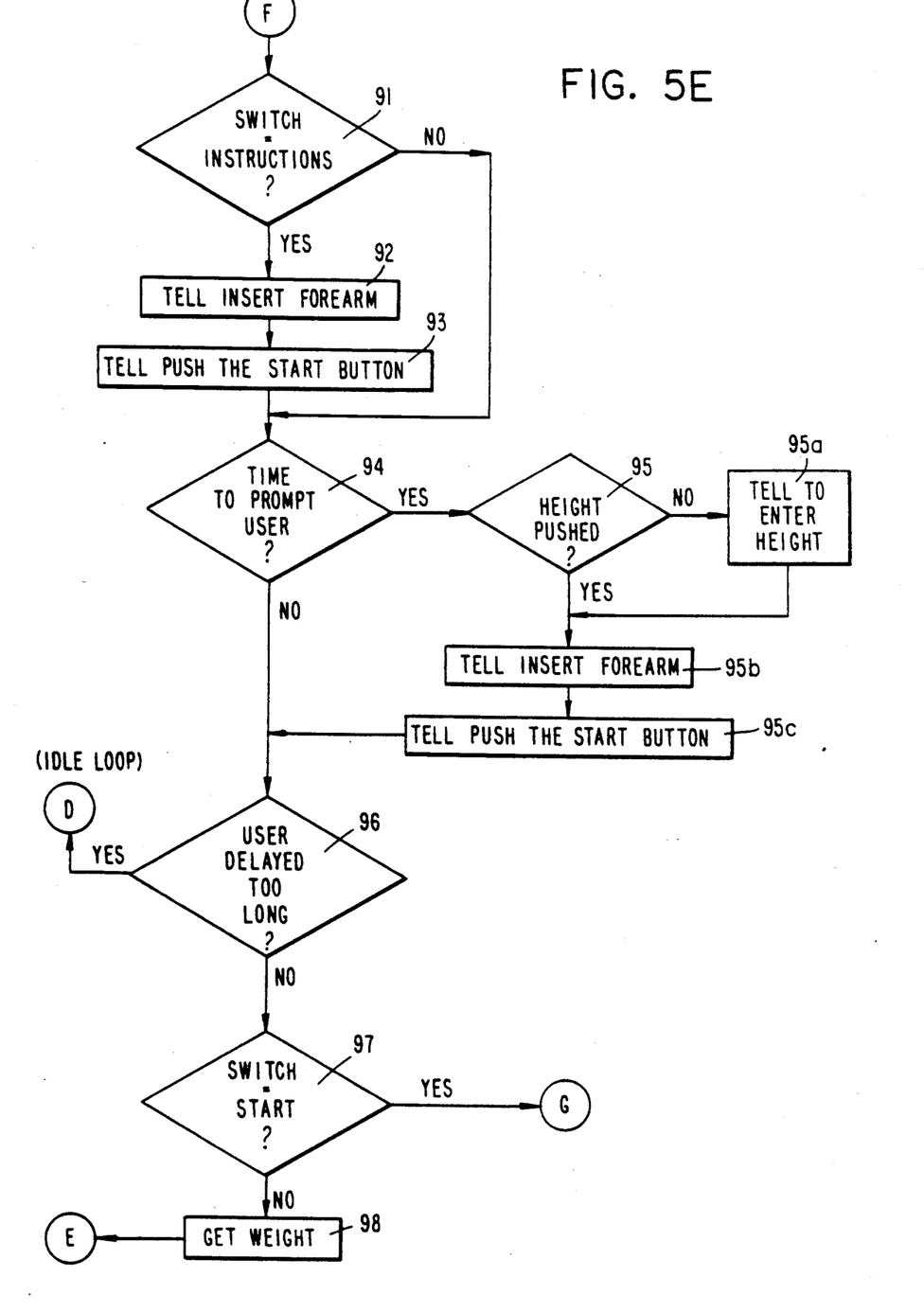

Referring now to FIG. 5E, the instructions switch is again interrogated and, in response, the user is instructed 92 to insert his or her forearm into the inflatable cuff and to press the start button 93. If instructions have not been requested, a timer is interrogated 94 to determine if the user should be prompted again. If this prompt is determined to be required, entry of height data is again tested 95 and a prompt to enter the same 95a is again issued, if necessary. The user is again prompted to insert his or her forearm into the inflatable cuff 95b and to press the start button 95c. If this is not done within a predetermined period, governed by a timer, the idle loop may again be entered at 96 by a branch to D in FIG. 5B. If height data has been entered, but the start switch has not been pushed, weight data, if provided, is obtained and the process is resumed at E of FIG. 5D which again allows for early termination of the test. If the start key has been actuated, a branch is made to G of FIG. 5F.

Figure 4:
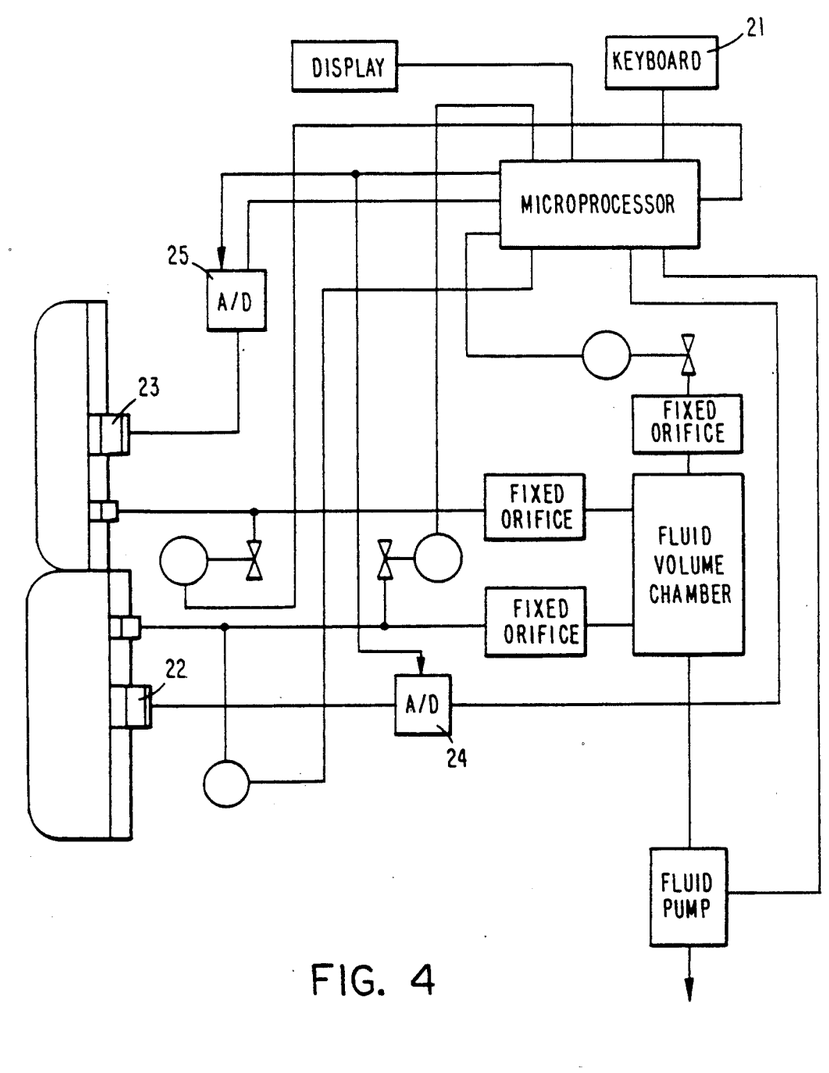
FIG. 4 is a schematic diagram according to a variation of the invention.
Figure 5F:
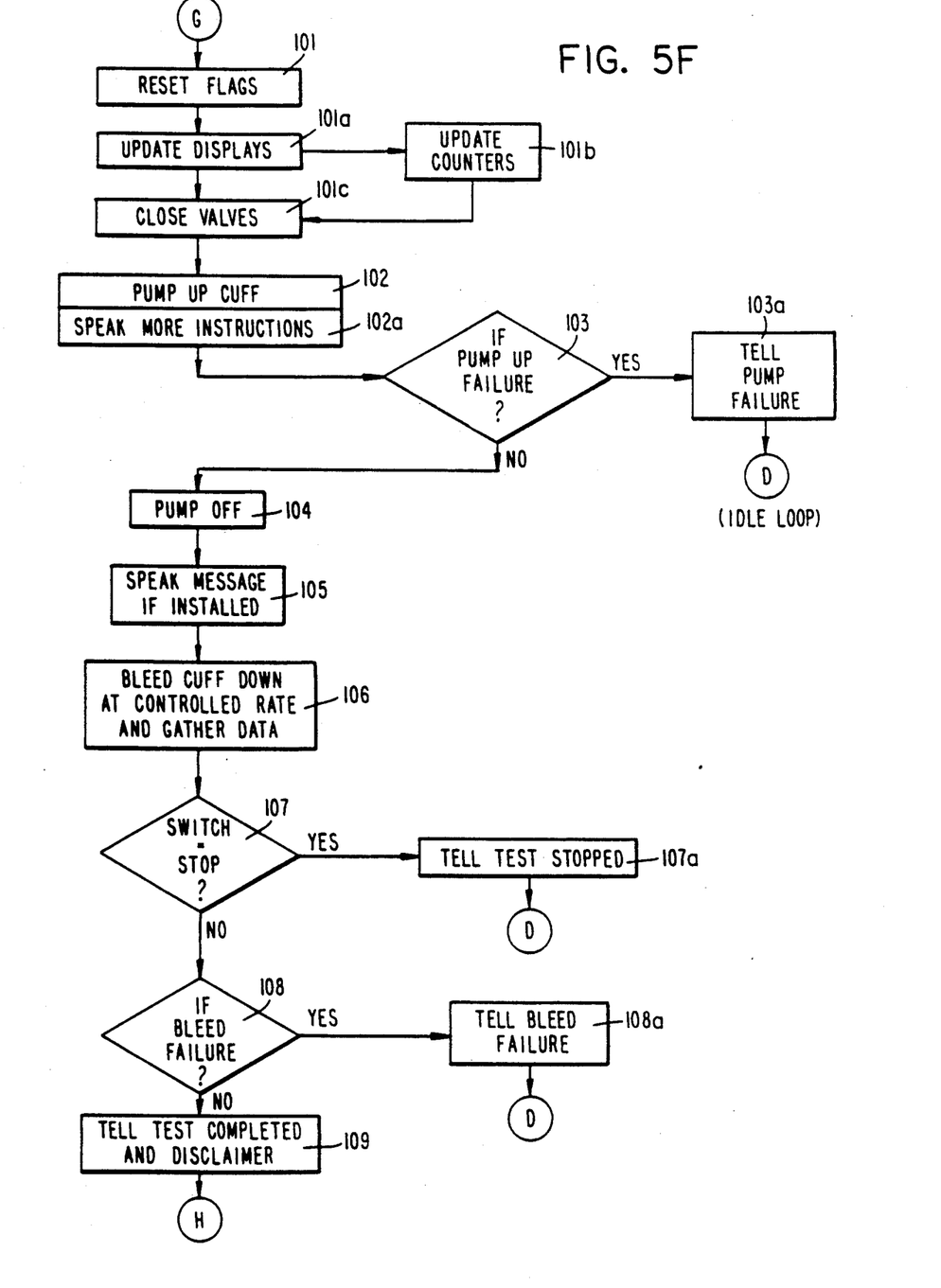

Referring now to FIG. 5F, the process of the blood pressure test is conducted. Flags are reset 101, displays are updated 101a, counters are updated 101b valves, shown in FIG. 3 or 4 are closed, as disclosed in U.S. Pat. No. 4,729,382, and inflation of the inflatable cuff is initiated 102. While the cuff is being inflated, further instruction or messages of reassurance may be issued (102a). Inflation is checked 103 and any malfunction is reported and the idle loop is resumed if the cuff inflation fails. If cuff inflation is successful, the pump is turned off 104 and any further installed message 105 is communicated and bleed down o the cuff and data gathering 106 is started.

At step 106, the user is given another opportunity to abort the test 107 while data is being collected at step 106. If the stop switch is now actuated, termination of the test is announced 107a and the idle loop is resumed at D. If the test is not stopped, the bleed down of the cuff is monitored 108 and if an error is detected, a bleed down failure is announced 108a and the idle loop is resumed at D of FIG. 5B. If the bleed down is successful, completion of the test is announced with other desired messages such as a disclaimer at step 109.

Figure 5G:
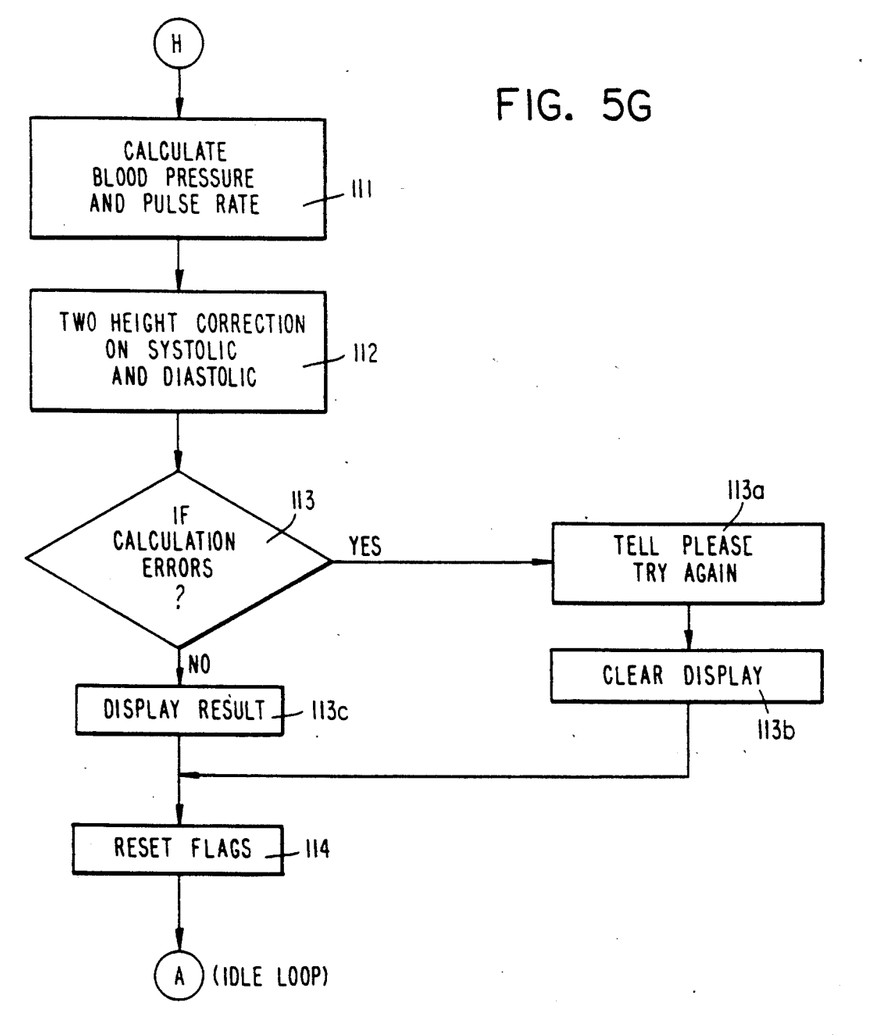

Referring now to FIG. 5G, the measured blood pressure (and pulse rate) are computed and fetched from A/D converters of FIG. 3, if used, at step 111. Correction data is now fetched from memory as specified by the keyboard or other data entry means and a correction is made at step 112, responsive thereto. Accuracy of the blood pressure, pulse rate and error correction computation is monitored at 113 and an error message is issued 113a and display is cleared (113b) if the correction is not properly performed. If no error is detected, results are displayed (113c). In either case, the test, whether or not successful, is now complete and flags are reset 114 and the idle loop is reentered through A of FIG. 5B.

According to the present invention, a keyboard which preferably includes a numerical keypad and a plurality of control switches, such as for turning off the voice-synthesized annunciation of instructions and results or controlling other options, thereof, is substituted for the start/stop switch of the cited device. Keyboard 13 may be advantageously selectively illuminated to prompt a user to enter data and to exercise control in a proper sequence as is well known in the art. Analog-to-digital converters are also provided to digitize the outputs of sensors 22 and 23. Memory 21 is also included, preferably in the form of a ROM chip possibly in the form of an EPROM used as a look-up table for the purpose of holding numerical data representing a correction relationship which has been either theoretically or empirically determined for providing correction numbers in mmHg to be subtracted from measured blood pressure values to correct for the hydrostatic pressure caused by differential heights 30b and 30c of FIGS. 2B and 2C, respectively. Memory 21 can also be a portion of memory storing the program for the microprocessor. The apparatus according to the preferred embodiment of the invention also includes display 19.

In operation, an operator will activate the apparatus by pressing a designated key of keyboard 13 to terminate a stand-by state of the apparatus. When this is done, the apparatus, under control of microprocessor 20 will prompt the user to enter his or her height either by display or voice annunciator. If this is not done after repeated prompts, a default at the minimum design height for a user is adopted. This feature provides a safety function since the output blood pressure value will be higher than if corrected since no correction is performed for a user of the minimum height for which the apparatus is intended. Alternatively, user height can be determined by direct measurement as by a mechanical arm or optical sensing in a manner well known in the art.

After data is obtained to specify the user's height, the test may be started by the user in the manner disclosed in U.S. Pat. No. 4,729,382. The user can also abort the test should inflation of the cuff be uncomfortable. The data obtained regarding the height of the user is used to address memory 21 which outputs correction numbers stored therein which are then subtracted from the digital outputs of analog-to-digital converters 24 and 25, responsive to sensors 22 and 23. The result of the measurement, thus corrected, is displayed on display 19.

The data held in memory 21 can be theoretically developed on the basis of a correction of an average variation of 1.5-2 mmHg per inch of height with a somewhat smaller correction for heights near the minimum design height and heights above 74", where postures similar to that of FIG. 2C will be assumed by the user. The data can also be determined empirically and the following Table I provides data which has been experimentally found to provide a good correlation with blood pressure measurements taken in more standard postures.

TABLE I

| Height of User | Correction |
| --- | --- |
| 62" | +2 mmHg |
| 64" | 0 |
| 66" | −2 |
| 68" | −6 |
| 70" | −9 |
| 72" | −12 |
| 74" | −14 |
| 76" | −16, etc. |

In an alternative embodiment, shown in FIG. 4, which is also similar to FIG. 1 of U.S. Pat. No. 4,728,382, the keyboard entry of height data to the microprocessor is used to control a multiplication factor of the analog-to-digital converters preferably in a non-linear manner which is, per se, well-known in the art. In this case, the output of the D/A converters will already be corrected for the height of the user and can be directly displayed under control of the microprocessor.

It should be noted from Table I above that corrections need only be provided for two inch increments of height to provide resolution of measurement which is well within accepted medical standards. For instance, the above table, when implemented in the invention has a mean accuracy ±3 mmHg which is the standard accepted by the AAMI (Association for Advancement of Medical Instrumentation). Most physicians accept a mean accuracy of ±10 mmHg for non-invasive testing. Since the total number of necessary correction data is small, the use of a look-up table is the preferred form of implementation of the invention although others, such as that of FIG. 4, discussed above and others, such as dedicated digital display decoders are certainly possible alternative means of accomplishing the numerical correction function.

It should also be noted from Table I that it may be desireable to provide additive corrections to allow for use by persons having a height slightly less than the design height of the apparatus since the apparatus of the invention can be used with reasonable comfort with the user's arm fully extended at shoulder height, yielding a hydrostatic reduction in measured blood pressure which must be compensated by increasing the measured value.

Other variations on the basic invention are also possible to improve the function and accuracy thereof, should different standards be required. For instance both the measured blood pressure and height data could be used together to address the look-up table to improve the ability of the invention to conform to empirical data. In this case, subtraction would not be necessary and the value obtained from the look-up table could be directly displayed. Other variables reflecting stature, such as weight, could also be utilized to used to obtain correction data.

Having thus fully described the invention, other variations will become apparent to those skilled in the art without departing from the spirit and scope of the present invention. For instance, as noted above, the apparatus of the invention may be combined with other transducers for independent or combined readout of other physical parameters such as weight; which parameters may also be interrelated under control of the microprocessor to provide a more detailed health and condition evaluation. Accordingly, it is intended that the above description of the invention be taken as by way of example and not of limitation, the scope of the invention being defined solely by the appended claims.

We claim:

1. In an apparatus for determining the blood pressure of a user, comprising an inflatable cuff means for encircling a portion of the user's body, an inflation means for controllably inflating and deflating said cuff means, pressure variation sensing means for monitoring blood circulation of said user during inflation and deflation of said cuff means, determining means responsive to said pressure variation sensing means for determining the blood pressure of said user including measuring means for measuring the diastolic and systolic blood pressure of said user and means for communicating the output of said determining means to said user, the improvement comprising:

data entry means for inputting data representative of a parameter of the physique of the user,
   wherein said determining means includes means responsive to said data entry means for applying a correction to the output of said measuring means to correct the output of said determining means.

2. An apparatus as defined in claim 1, wherein the improvement further comprises
   said determining means comprises a programmed microprocessor means and said data entry means includes memory means for storing correction values.

3. An apparatus as defined in claim 2, wherein the improvement further comprises
   said data entry means comprises a keyboard.

4. An apparatus as defined in claim 2, wherein the improvement further comprises
   a support means for supporting said apparatus
   a mounting means for mounting said inflatable cuff means to at least one of said apparatus and said support means,
   said support means including means for supporting at least one of said apparatus and said inflatable cuff means at a height suitable for the insertion of the lower arm of the user while said user is in a standing posture.

5. An apparatus as defined in claim 4, wherein the improvement further comprises
   said data entry means further includes weight measurement means for measuring the weight of said user.

6. A method of for measuring the blood pressure of a user by the use of automated apparatus, said apparatus including an inflatable cuff means for encircling a portion of the user's body, an inflation means for controllably inflating and deflating said cuff means, pressure variation sensing means for monitoring blood circulation of said user during inflation and deflation of said cuff means, determining means responsive to said pressure variation sensing means for determining the blood pressure of said user including measuring means for measuring the diastolic and systolic blood pressure of said user and means for communicating the output of said determining means to said user, comprising the steps of
   a. operating said data entry means to enter data corresponding to the height of said user,
   b. inserting the lower arm of the user within said inflatable cuff means,
   c. causing said apparatus to measure the blood pressure of said user,
   d. correcting the output of said determining means in accordance with said data corresponding to said height of said user to derive a corrected result and
   e. displaying said corrected result.

7. A method of correcting a blood pressure measurement for the posture of a user of a blood pressure measurement apparatus having an inflatable cuff means at a predetermined height relative to a support for said user comprising the steps of
   establishing a correction relationship between at least average heights of heart levels relative to user heights and said predetermined height and measured blood pressure values measured in a standard posture,
   obtaining data representing the height of said user,
   measuring the blood pressure of said user to derive a measurement result,
   correcting said measurement result according to said correction relationship to obtain a corrected measurement value and
   communicating said corrected measurement value to said user.

8. A blood pressure measurement apparatus comprising in combination:
   an inflatable cuff for encircling a portion of a user and mounted at a predetermined height relative to a support for said user,
   inflation means for controllably inflating and deflating said inflatable cuff,
   pressure measuring means responsive to variations in pressure in said cuff during said inflating and deflating thereof and providing a measurement result,
   means for providing data representing an overall height of said user above said support for said user in a predetermined posture determined by said predetermined height of said inflatable cuff and said support for said user,
   means for providing a correction relationship between average blood pressure of a typical user in said predetermined posture and a standard posture,
   means for correcting said measurement result based upon said overall height data of said user and said correction relationship and providing a corrected measurement value and means for communicating said corrected measurement value to said user.

9. An appatatus as defined in claim 8, wherein
said means for correcting said measurement result comprises a programmed microprocessor means and said means for providing a correction relationship includes memory means for storing correction values.

10. An apparatus as defined in claim 9, wherein said means for providing data comprises a keyboard.

11. An apparatus as defined in claim 10, further comprising
a support means for supporting said apparatus
a mounting means for mounting said inflatable cuff means to at least one of said apparatus and said support means,
said support means including means for supporting at least one of said apparatus and said inflatable cuff means at a height suitable for the insertion of the lower arm of the user while said user is in a standing posture.

12. An apparatus as defined in claim 11, wherein said means for providing data further includes weight measurement means for measuring the weight of said user.

13. In a method of measuring blood pressure of a user of a blood pressure measuring apparatus, an improvement comprising the steps of
providing data representing the a physical parameter of the body of said user,
providing a correction relation based on said physical parameter,
correcting measured blood pressure responsive to said data to provide corrected blood pressure, and
communicating said corrected blood pressure data to said user.

* * * * *